United States Patent [19]

Wiedemann et al.

[11] Patent Number: 4,503,067

[45] Date of Patent: Mar. 5, 1985

[54] CARBAZOLYL-(4)-OXYPROPANOLAMINE COMPOUNDS AND THERAPEUTIC COMPOSITIONS

[75] Inventors: Fritz Wiedemann, Weinheim-Lützelsachsen; Wolfgang Kampe, Heddesheim; Max Thiel, Mannheim; Gisbert Sponer, Hemsbach; Egon Roesch, Mannheim; Karl Dietmann, Mannheim-Vogelstang, all of Fed. Rep. of Germany

[73] Assignee: Boehringer Mannheim GmbH, Mannheim-Waldhof, Fed. Rep. of Germany

[21] Appl. No.: 479,921

[22] Filed: Apr. 4, 1983

Related U.S. Application Data

[63] Continuation of Ser. No. 198,975, Oct. 21, 1980, abandoned, which is a continuation of Ser. No. 21,394, Mar. 16, 1979, abandoned.

[30] Foreign Application Priority Data

Apr. 13, 1978 [DE] Fed. Rep. of Germany ....... 2815926

[51] Int. Cl.³ .................. A61K 31/40; C07D 401/12; C07D 209/82
[52] U.S. Cl. .................................. 514/411; 546/272; 548/444; 514/339
[58] Field of Search ............... 424/263, 274, 198, 975; 546/272; 548/444

[56] References Cited

U.S. PATENT DOCUMENTS

| | | | |
|---|---|---|---|
| 1,834,015 | 12/1931 | Ballauf et al. | 260/315 |
| 2,944,058 | 7/1960 | Kallischnigg | 546/272 X |
| 3,846,445 | 11/1974 | Bondesson et al. | 260/315 |
| 3,932,424 | 1/1976 | Albrecht et al. | 260/315 X |
| 3,975,398 | 8/1976 | Werner et al. | 260/315 |
| 3,976,779 | 8/1976 | Leinert et al. | 260/315 X |
| 3,998,810 | 12/1976 | Wiedemann et al. | 260/315 X |
| 4,076,829 | 2/1978 | Kampe et al. | 260/326.13 R X |
| 4,086,357 | 4/1978 | Large et al. | 260/315 X |
| 4,115,409 | 9/1978 | Large et al. | 260/315 X |
| 4,152,446 | 5/1979 | Kampe et al. | 424/274 |

FOREIGN PATENT DOCUMENTS 2424523 12/1975 Fed. Rep. of Germany ...... 260/315

OTHER PUBLICATIONS

Ulrych et al., Circulation 37, 411–416 (1968).
Kaplan, N.M., Clinical Hypertension, 2nd ed. pp.125–128.
Waal, H.J. Clinical Pharmacology and Therapeutics vol. 7, 588–598 (1966).
J.A.M.A 237, 2303–2310 (1977).
Gilmore, E. et al., The New England Journal of Medicine 282, 521–527 (1970).
Zacest, R., et al. The New Journal of Medicine 286, 617–622 (1972).
Weiner, N., The Pharmacological Basis of Therapeutics (1980) Chap. 9, pp. 176, 188, 191, 194.
Conway et al., Medical Science and Molecular Medicine 48, 101s–103s (1975).

Primary Examiner—Joseph Paul Brust
Attorney, Agent, or Firm—Felfe & Lynch

[57] ABSTRACT

Carbazolyl-(4)-oxypropanolamine compounds of the formula

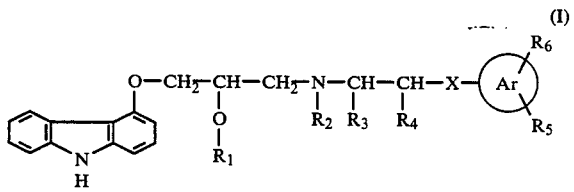

wherein
$R_1$ is hydrogen, lower alkanoyl or aroyl;
$R_2$ is hydrogen, lower alkyl or arylalkyl;
$R_3$ is hydrogen or lower alkyl;
$R_4$ is hydrogen or lower alkyl, or when X is oxygen, $R_4$ together with $R_5$ can represent $-CH_2-O-$;
X is a valency bond, $-CH_2-$, oxygen or sulfur;
Ar is mono- or bicyclic aryl or pyridyl;
$R_5$ and $R_6$ are individually selected from hydrogen, halogen, hydroxyl, lower alkyl, aminocarbonyl, lower alkoxy, aralkyloxy, lower alkylthio, lower alkylsulphinyl or lower alkylsulphonyl;
$R_5$ and $R_6$ together can represent methylenedioxy;

and the salts thereof with physiologically acceptable acids are outstandingly effective in the treatment and prophylaxis of circulatory and cardiac diseases, e.g., hypertension and angina pectoris.

18 Claims, No Drawings

CARBAZOLYL-(4)-OXYPROPANOLAMINE COMPOUNDS AND THERAPEUTIC COMPOSITIONS

This application is a continuation of Ser. No. 198,975, filed Oct. 21, 1980 (abandoned) which in turn is a continuation of Ser. No. 021,394, filed Mar. 16, 1979 (abandoned).

The present invention is concerned with new carbazolyl-(4)-oxypropanolamine compounds, and pharmaceutical compositions containing them. In addition, the invention relates to methods for the treatment and prophylaxis of circulatory and cardiac diseases, e.g., hypertension and angina pectoris.

The carbazolyl-(4)-oxypropanolamine compounds of the present invention are compounds of the formula:

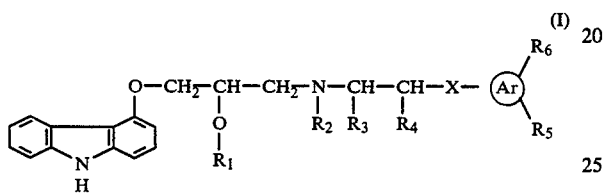

wherein
$R_1$ is hydrogen, lower alkanoyl or aroyl;
$R_2$ is hydrogen, lower alkyl or arylalkyl;
$R_3$ is hydrogen or lower alkyl;
$R_4$ is hydrogen or lower alkyl, or when X is oxygen, $R_4$ together with $R_5$ can represent —$CH_2$—O—;
X is a valency bond, —$CH_2$—, oxygen or sulfur;
Ar is mono- or bicyclic aryl or pyridyl;
$R_5$ and $R_6$ are individually selected from hydrogen, halogen, hydroxyl, lower alkyl, aminocarbonyl, lower alkoxy, aralkyloxy, lower alkylthio, lower alkylsulphinyl or lower alkylsulphonyl;
$R_5$ and $R_6$ together can represent methylenedioxy; and the salts thereof with physiologically acceptable acids.

The lower alkyl radicals of the substituents $R_2$, $R_3$, $R_4$, $R_5$ and $R_6$ contain up to 6 and preferably up to 4 carbon atoms and can be straight-chained or branched. Preferred alkyl radicals are the methyl, ethyl, isopropyl, tert.-butyl and n-butyl radicals.

The lower alkanoyl radicals contain up to 6 carbon atoms, preferred alkanoyl radicals being the formyl, acetyl, propioryl and pivaloyl radicals.

The aroyl radicals are preferably the benzoyl and naphthoyl radicals.

A preferred arylalkyl radical is the benzyl radical but it can also be, for example, a phenylethyl or phenylpropyl radical.

The halogen atom is to be understood to be a fluorine, chlorine or bromine atom.

A lower alkoxy, alkylthio, alkylsulphinyl or alkylsulphonyl radical can contain up to 6 and preferably up to 4 carbon atoms, the preferred radicals being the methoxy, ethoxy, methylthio, methylsulphinyl and methylsulphonyl radicals.

The aralkyloxy radical is preferably a benzyloxy radical.

When Ar is a bicyclic aryl radical, a ring can also be partly hydrogenated. Preferred radicals include the phenyl, naphthyl, indanyl and tetrahydronaphthyl radicals.

An example of a radical in which $R_4$ and $R_5$ together form a —$CH_2$—O— radical, when X is an oxygen atom, is the 1,4-benzodioxanyl-(2)-methyl radical.

The compounds of general formula (I) and the physiologically acceptable salts thereof show, in pharmacological tests, vasodilatory and β-receptor-blocking actions. They are, therefore, suitable for the treatment and prophylaxis of circulatory and cardiac diseases, for example of hypertension and angina pectoris.

German Patent Specification No. 2,240,599 describes carbazole derivatives which block the activity of the β-receptors of the sympathicus.

The new compounds according to the present invention can be prepared, for example, by one of the following methods:

(a) reaction of a compound of the general formula:

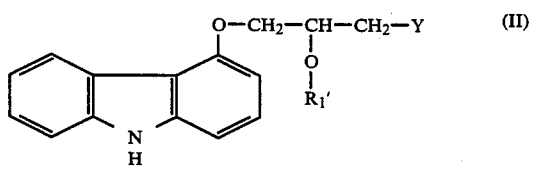

wherein Y is a reactive group and $R_1'$ has the same meaning as given above for $R_1$ or Y and $R_1'$ together signify a valency bond, with a compound of the general formula:

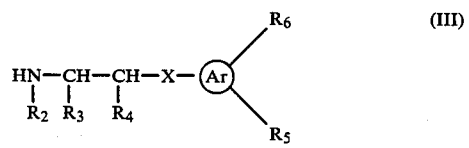

wherein $R_2$, $R_3$, $R_4$, X, Ar, $R_5$ and $R_6$ have the same meanings as above; or (b) reaction of a compound of the general formula:

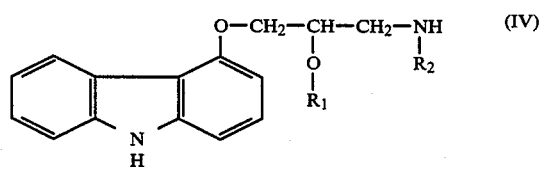

wherein $R_1$ and $R_2$ have the same meanings as above, with a compound of the general formula:

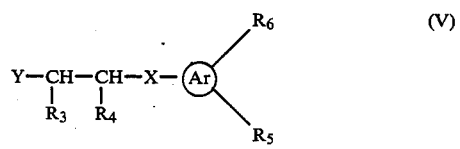

wherein Y, $R_3$, $R_4$, X, Ar, $R_5$ and $R_6$ have the same meanings as above; or (c) reduction of a mixture of a compound of general formula (IV) and of a compound of the general formula:

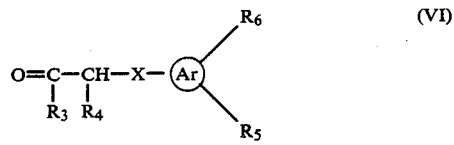

in which R$_3$, R$_4$, X, Ar, R$_5$ and R$_6$ have the same meanings as above; or (d) reaction of a compound of general formula (IV) with a compound of the general formula:

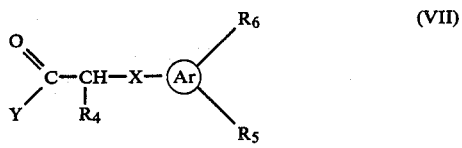

in which Y, R$_4$, X, Ar, R$_5$ and R$_6$ have the same meanings as above, and the amide obtained is reduced, whereupon, if desired, the compound thus obtained of general formula (I) is converted into a different compound of general formula (I) and, if desired, a compound obtained is converted into a pharmacologically acceptable salt.

Reactive groups Y of the compounds of general formulae (II), (V) and (VII) are preferably acid residues, for example of hydrohalic acids or of sulphonic acids.

Processes (a) and (b) according to the present invention are preferably carried out in an organic solvent which is inert under the reaction conditions, for example, toluene, dioxan, ethylene glycol dimethyl ether, isopropanol or dimethylformamide, optionally in the presence of an acid-binding agent. The reaction of an epoxide of general formula (II) (Y and R' together represent a valency bond) with an amine of general formula (III) can, however, also be accomplished after mixing the reaction components, by leaving the reaction mixture to stand at ambient temperature or by heating. According to process (c), an amine of general formula (IV) is hydrogenated with a carbonyl compound of general formula (VI) in an inert solvent, for example methanol, in the presence of a catalyst, for example Raney nickel.

The amides obtained according to process (d) are preferably reduced by means of complex metal hydrides, for example lithium aluminium hydride.

Compounds of general formula (I) in which R$_1$ is a hydrogen atom can be esterified by reaction with an acid halide or acid anhydride, possibly in the presence of an acid-binding agent, for example, pyridine or triethylamine, and benzyl protective groups possibly present can be removed by catalytic hydrogenation in the presence of noble metal catalysts.

The starting compounds employed in the processes according to the present invention are, as a rule, known from the literature. The new compounds can generally be obtained analogously to the processes known for the preparation of the known compounds. Thus, amines of general formula (III) are preferably prepared by reacting haloalkyl nitriles with appropriate phenols, naphthols or aryl compounds, for example chloroacetonitrile and phenol, with subsequent hydrogenation in the presence of ammonia.

The amines of general formula (IV) can be obtained from the known 4-(2,3-epoxypropoxy)-carbazole (cf. German Patent Specification No. 2,240,599) by reaction with liquid ammonia.

Reactive compounds of general formula (V), for example p-toluenesulphonic acid esters, are, as a rule, prepared from the appropriate phenols, naphthols or aryl compounds by reaction with haloalcohols and subsequent esterification with p-toluenesulphonic acid.

The carbonyl compounds of general formula (VI) and acid chlorides of general formula (VII) are obtained from the appropriate phenols, naphthols and aryl compounds by reaction with appropriate haloalkyl compounds.

A subsequent conversion of a compound of general formula (I) into another compound of general formula (I) can take place, for example, by oxidation, for example conversion of an alkylthio radical into an alkylsulphinyl or alkylsulphonyl radical. Furthermore, hydroxyl groups can be etherified or esterified according to known methods or, on the other hand, ester and ether groups can be converted into hydroxyl groups.

For the conversion of compounds of general formula (I) into their pharmacologically acceptable salts, these are reacted, preferably in an organic solvent, with an equivalent amount of an inorganic or organic acid, for example, hydrochloric acid, hydrobromic acid, phosphoric acid, sulphuric acid, acetic acid, citric acid, maleic acid or benzoic acid.

The compounds of general formula (I) according to the present invention can be resolved by known methods, via diastereomeric salts, into the optically-active forms. For the resolution of the racemates, there can be used, for example, tartaric acid, malic acid, camphoric acid or camphorsulphonic acid.

For the preparation of pharmaceuticals, the new compounds according to the present invention are mixed in the usual manner with appropriate pharmaceutical carrier materials and aroma, flavoring and coloring materials are formed, for example, into tablets or dragees or, with the addition of appropriate adjuvants, suspended or dissolved in water or in an oil, for example, olive oil.

The new compounds (I) according to the present invention and the salts thereof can be administered enterally or parenterally in liquid or solid form. As injection medium, it is preferable to use water which contains the additives usual in the case of injection solutions, such as stabilizing agents, solubilizing agents and/or buffers. Additives of this type include, for example, tartrate and citrate buffers, ethanol, complex-forming agents (such as ethylenediaminetetraacetic acid and the non-toxic salts thereof) and high molecular weight polymers (such as liquid polyethylene oxide) for viscosity regulation. Solid carrier materials are, for example starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening materials.

The following Examples are given for the purpose of illustrating the present invention:

EXAMPLE 1

1-[Carbazolyl-(4)-oxy]-3-[2-(2-methoxyphenyl)-ethylamino]-propan-2-ol 6.0 g. 4-(2,3-Epoxypropoxy)-carbazole and 7.6 g. 2-(2-methoxyphenyl)-ethylamine are stirred for 20 hours at 70° C. The reaction mixture is then triturated with diethyl ether, filtered with suction and recrystallized from ethyl acetate, with the use of active charcoal and fullers' earth. There are obtained 6.0 g. (61% of theory) of the desired compound in the form of colorless crystals; m.p. 135°–136° C.

The following compounds are obtained in an analogous manner:

(a)
1-[carbazolyl-(4)-oxy]-3-[2-(3,4-dimethoxyphenyl)-ethylamino]-propan-2-ol Yield 42% of theory; m.p. 129°–130° C.; acetate m.p. 180°–183° C.,
from 4-(2,3-epoxypropoxy)-carbazole and 2-(3,4-dimethoxyphenyl)-ethylamine.

(b)
1-[carbazolyl-(4)-oxy]-3-[2-(2-pyridyl)-ethylamino]-propan-2-ol yield 32% of theiry; m.p. 105°–107° C.,
from 4-(2,3-epoxypropoxy)-carbazole and 2-(2-pyridyl)-ethylamine.

(c)
1-[carbazolyl-(4)-oxy]-3-[2-(4-pyridyl)-ethylamino]-propan-2-ol yield 24% of theory; m.p. 86°–88° C.,
from 4-(2,3-epoxypropoxy)-carbazole and 2-(4-pyridyl)-ethylamine.

(d)
1-[carbazolyl-(4)-oxy]-3-(3-phenylpropylamino)-propan-2-ol yield 30% of theory; succinate m.p. 98°–99° C.,
from 4-(2,3-epoxypropoxy)-carbazole and 3-phenylpropylamine.

(e)
1-[carbazolyl-(4)-oxy]-3-[4-phenylbutyl-(2)-amino]-propan-2-ol yield 13% of theory; m.p. 124°–125° C.,
from 4-(2,3-epoxypropoxy)-carbazole and 4-phenylbutyl-(2)-amine.

EXAMPLE 2

1-[Carbazolyl-(4)-oxy]-3-[2-(2-methoxyphenoxy)-ethylamino]-propan-2-ol 22.6 g. 4-(2,3-Epoxypropoxy)-carbazole and 17.4 g. 2-(2-methoxyphenoxy)-ethylamine in 75 ml. ethylene glycol dimethyl ether are stirred for 25 hours at 50° C. The reaction mixture is evaporated to dryness in a Rotavapor and the residue is triturated with diethyl ether and recrystallized from ethyl acetate, with the use of active charcoal. There are obtained 15.1 g. (39% of theory) of the desired compound in the form of colorless crystals; m.p. 114°–115° C.

The following compounds are obtained in an analogous manner:

(a)
1-[carbazolyl-(4)-oxy]-3-(2-phenoxyethylamino)-propan-2-ol yield 32% of theory; m.p. 105°–107° C.,
from 4-(2,3-epoxypropoxy)-carbazole and 2-phenoxyethylamine.

(b)
1-[carbazolyl-(4)-oxy]-3-[1-phenoxypropyl-(2)-amino]-propan-2-ol yield 31% of theory; hydrochloride m.p. 116°–119° C.,
from 4-(2,3-epoxypropoxy)-carbazole and 1-phenoxypropyl-(2)-amine.

(c)
1-[carbazolyl-(4)-oxy]-3-[1,4-benzodioxanyl-(2)-methylamino]-propan-2-ol yield 28% of theory; m.p. 129°–131° C.,
from 4-(2,3-epoxypropoxy)-carbazole and 2-(aminomethyl)-1,4-benzodioxan.

(d)
1-[carbazolyl-(4)-oxy]-3-[2-(4-carbamoylphenoxy)-ethylamino]-propan-2-ol yield 13% of theory; m.p. 120°–122° C.,
from 4-(2,3-epoxypropoxy)-carbazole and 2-(4-carbamoylphenoxy)-ethylamine.

EXAMPLE 3

1-[Carbazolyl-(4)-oxy]-3-[2-(2-ethoxyphenoxy)-ethylamino]-propan-2-ol 6.0 g. 4-(2,3-Epoxypropoxy)-carbazole and 9.1 g. 2-(2-ethoxyphenoxy)-ethylamine are stirred for 20 hours at 70° C. After cooling, the reaction mixture is stirred with diethyl ether, filtered with suction and the residue recrystallized from ethyl acetate, with the use of active charcoal and fullers' earth. The yield is 4.4 g. (42% of theory) of the desired compound in the form of colorless crystals; m.p. 127.5°–128.5° C.

The following compounds are obtained in an analogous manner:

(a)
1-[carbazolyl-(4)-oxy]-3-[2-(4-fluorophenoxy)-ethylamino]-propan-2-ol yield 56% of theory; m.p. 145°–146° C.,
from 4-(2,3-epoxypropoxy)-carbazole and 2-(4-fluorophenoxy)-ethylamine.

(b)
1-[carbazolyl-(4)-oxy]-3-[2-(4-tert.-butylphenoxy)-ethylamino]-propan-2-ol yield 51% of theory; m.p. 127°–128° C.,
from 4-(2,3-epoxypropoxy)-carbazole and 2-(4-tert.-butylphenoxy)-ethylamine.

(c)
1-[carbazolyl-(4)-oxy]-3-[2-(2,3-dimethylphenoxy)-ethylamino]-propan-2-ol yield 51% of theory; m.p. 128°–129° C.,
from 4-(2,3-epoxypropoxy)-carbazole and 2-(2,3-dimethylphenoxy)-ethylamine.

(d)
1-[carbazolyl-(4)-oxy]-3-{2-[indanyl-(5)-oxy]-ethylamino}-propan-2-ol yield 54% of theory; m.p. 143°–145° C.,
from 4-(2,3-epoxypropoxy)-carbazole and 2-[indanyl-(5)-oxy]-ethylamine.

(e)
1-[carbazolyl-(4)-oxy]-3-{2-[naphthyl-(1)-oxy]-ethylamino}-propan-2-ol yield 64% of theory; m.p. 116°–119° C.,
from 4-(2,3-epoxypropoxy)-carbazole and 2-[naphtyl-(1)-oxy]-ethylamine.

(f)
1-[carbazolyl-(4)-oxy]-3-[2-(3,4-methylenedioxyphenoxy)-ethylamino]-propan-2-ol yield 32% of theory; m.p. 142°–143° C.,
from 4-(2,3-epoxypropoxy)-carbazole and 2-(3,4-methylenedioxyphenoxy)-ethylamine.

(g)
1-[carbazolyl-(4)-oxy]-3-[2-(2,6-dimethoxyphenoxy)-ethylamino]-propan-2-ol yield 65% of theory; m.p. 136°–138° C.,
from 4-(2,3-epoxypropoxy)-carbazole and 2-(2,6-dimethoxyphenoxy)-ethylamine.

(h)
1-[carbazolyl-(4)-oxy]-3-[2-(2-methoxyphenoxy)-propylamino]-propan-2-ol yield 83% of theory; m.p. 137°–157° C. (crude mixture of the diastereomers); from this, by two recrystallizations from ethyl acetate; 22% of theory; m.p. 173°–175° C.,
from 4-(2,3-epoxypropoxy)-carbazole and 2-(2-methoxyphenoxy)-propylamine.

(i)
1-[carbazolyl-(4)-oxy]-3-[2-(2-methylthiophenoxy)-ethylamino]-propan-2-ol yield 40% of theory; m.p. 83°–85° C.,
from 4-(2,3-epoxypropoxy)-carbazole and 2-(2-metylthiophenoxy)-ethylamine.

(j)
1-[carbazolyl-(4)-oxy]-3-[2-(2-benzyloxyphenoxy)-ethylamino]-propan-2-ol yield 56% of theory; m.p. 138°–139° C.,
from 4-(2,3-epoxypropoxy)-carbazole and 2-(2-benzyloxyphenoxy)-ethylamine.

The starting amines employed in Examples 3c, 3d, 3f, 3g and 3i can be prepared via the corresponding nitriles by processes analogous to those described in the literature.

2,3-Dimethylphenoxyacetonitrile 100 g. 2,3-Dimethylphenol, 57 ml. chloroacetonitrile, 110 g. potassium carbonate and 2.0 g. potassium iodide are stirred under reflux for 5 hours in 300 ml. methyl ethyl ketone. The reaction mixture is filtered off with suction, the filtrate is evaporated and the residue is distilled to give 88.0 g. 2,3-dimethylphenoxyacetonitrile in the form of a colorless oil; b.p. 137°–142° C./13 mm.Hg.

In an analogous manner, by the reactions of 5-indanole, 3,4-methylenedioxyphenol and 2-(methylthio)-phenol, respectively, with chloroacetonitrile, there are obtained the following compounds:
indanyl-(5)-oxyacetonitrile; b.p. 162°–165° C./14 mm.Hg.;
3,4-methylenedioxyphenoxyacetonitrile; b.p. 170°–175° C./12 mm.Hg.;
2-methylthiophenoxyacetonitrile; m.p. 56°–58° C.; b.p. 173°–176° C./12 mm.Hg.

2-[indanyl-(5)-oxy]-ethylamine 109 g. Indanyl-(5)-oxyacetonitrile are hydrogenated in the presence of Raney nickel in 700 ml. ethanol and 180 ml. liquid ammonia at 110 ats. and 90° C. After distillation of the reaction mixture, there are obtained 86 g. 2-[indanyl-(5)-oxy]-ethylamine in the form of a colorless oil; b.p. 154°–156° C./12 mm.Hg.

In an analogous manner, by hydrogenating 2,3-dimethylphenoxyacetonitrile or 3,4-methylenedioxyphenoxyacetonitrile, there are obtained the following compounds:
2-(2,3-dimethylphenoxy)-ethylamine; b.p. 129°–132° C./12 mm.Hg.;
2-(3,4-methylenedioxyphenoxy)-ethylamine; b.p. 162°–164° C./13 mm.Hg.

2-(2-methylthiophenoxy)-ethylamine 26.7 g. (2-Methylthiophenoxy)-acetonitrile are reduced with 8.5 g. lithium aluminium hydride in 1.3 liters diethyl ether by heating under reflux for 4 hours. After working up the reaction mixture in the usual manner and distilling, there are obtained 21.0 g. 2-(2-methylthiophenoxy)-ethylamine in the form of a colourless oil; b.p. 117°–120° C./0.1 mm.Hg.

In an analogous manner, by the reduction of 2,6-dimethoxyphenoxyacetonitrile, there is obtained the following compound:
2-(2,6-dimethoxyphenoxy)-ethylamine; b.p. 160°–162° C./12 mm.Hg.

EXAMPLE 4

1-[Carbazolyl-(4)-oxy]-3-[2-(2-methylphenoxy)-ethylamino]-propan-2-ol 6.0 g. 4-(2,3-Epoxypropoxy)-carbazole and 7.6 g. 2-(2-methylphenoxy)-ethylamine are stirred for 20 hours at 70° C. The reaction mixture is then dissolved in methylene chloride and the mixture separated by chromatography on a silica gel column (500 ml.) with the elution agents methylene chloride, methylene chloride-ethyl acetate (9:1 v/v and 7:3 v/v), ethyl acetate and ethyl acetate-methanol (9:1 v/v). The sequence of the elution is: tertiary amine, secondary amine and primary starting amine. After trituration with diethyl ether and recrystallization from ethyl acetate, with the use of active charcoal and fullers' earth, there are obtained 5.2 g. (53% of theory) of the desired compound in the form of colorless crystals; m.p. 125°–126° C.

The following compounds are obtained in an analogous manner:

(a)
1-[carbazolyl-(4)-oxy]-3-[2-(3-methylphenoxy)-ethylamino]-propan-2-ol yield 43% of theory: m.p. 129°–130° C.,
from 4-(2,3-epoxypropoxy)-carbazole and 2-(3-methylphenoxy)-ethylamine.

(b)
1-[carbazolyl-(4)-oxy]-3-[2-(2-chlorophenoxy)-ethylamino]-propan-2-ol yield 26% of theory; m.p. 111°–112° C.,
from 4-(2,3-epoxypropoxy)-carbazole and 2-(2-chlorophenoxy)-ethylamine.

(c)
1-[carbazolyl-(4)-oxy]-3-[2-(3-methoxyphenoxy)-ethylamino]-propan-2-ol yield 22% of theory; m.p. 111°–113° C.,
from 4-(2,3-epoxypropoxy)-carbazole and 2-(3-methoxyphenoxy)-ethylamine.

(d)
1-[carbazolyl-(4)-oxy]-3-[2-(4-methoxyphenoxy)-ethylamino]-propan-2-ol yield 48% of theory; m.p. 106°–108° C.,
from 4-(2,3-epoxypropoxy)-carbazole and 2-(4-methoxyphenoxy)-ethylamine.

(e)
1-[carbazolyl-(4)-oxy]-3-[2-(2-methoxyphenylthio)-ethylamino]-propan-2-ol yield 15% of theory; m.p. 108°–109° C.,
from 4-(2,3-epoxypropoxy)-carbazole and 2-(2-methylphenylthio)-ethylamine.

(f)
1-[carbazolyl-(4)-oxy]-3-[1-(2-methoxyphenoxy)-propyl-2-amino]-propan-2-ol yield 85% of theory; m.p. 112°–125° C. (crude mixture of the diastereomers), and from this, by recrystallization from ethanol, ethyl acetate and toluene-isopropanol, colorless crystals (m.p. 140°–141° C.) and from the mother liquor a further product (m.p. 121.5°–122.5° C.), from 4-(2,3-epoxypropoxy)-carbazole and 1-(2-methoxyphenoxy)-propyl-2-amine.

(g)
1-[carbazolyl-(4)-oxy]-3-[2-methylsulphinyulphenoxy)-ethylamino]-propan-2-ol yield 25% of theory; oxalate decomposes above 126° C.,
from 4-(2,3-epoxypropoxy)-carbazole and 2-(2-methylsulphinylphenoxy)-ethylamine.

The compound is also obtained by the oxidation of 1-[carbazolyl-(4)-oxy]-3-[2-(2-methylthiophenoxy)-ethylamino]-propan-2-ol (cf. Example 3i) with the equivalent amount of hydrogen peroxide in acetic acid at ambient temperature.

The starting amines used in Examples 4e, 4f and 4 g can be prepared by reactions analogous to those described in the literature as follows:

2-(2-methoxyphenylthio)-ethylamine by the reaction of o-(2-chloroethylthio)-anisole in liquid ammonia for 8 hours at 120° C.; oil; b.p. 118°–122° C./0.05 mm.Hg.; hydrochloride m.p. 163°–167° C.;

1-(2-methoxyphenoxy)-propyl-2-amine by the hydrogenation of 2-methoxyphenoxyacetone in ammonia-ethanol at 120 ats. and 90° C.; oil; b.p. 144°–146° C./13 mm.Hg.; oxalate m.p. 199°–200° C. (decomp.);

2-(2-methylsulphinylphenoxy)-ethylamine by the oxidation of 2-(2-methylthio)-ethylamine with one equivalent of perhydrol (30%) in acetic acid at ambient temperature; oil; oxalate m.p. 174°–175° C.

EXAMPLE 5
1-[carbazolyl-(4)-oxy]-3-[N-benzyl-2-(2-methoxyphenoxy)-ethylamino]-propan-2-ol 15.1 g. 4-(2,3-Epoxypropoxy)-carbazole and 16.2 g. N-[2-(2-methoxyphenoxy)-ethyl]-benzylamine in 50 ml. ethylene glycol dimethyl ether are heated under reflux for 24 hours. The reaction mixture is evaporated to dryness, the residue is purified over a silica gel column with the elution agents methylene chloride, methylene chloride-ethyl acetate (9:1 v/v and 7:3 v/v) and ethyl acetate and the residue obtained by evaporation of the main fraction is triturated with diethyl ether. There are obtained 25.0 g. (80% of theory) of the desired compound in the form of colorless crystals; m.p. 97°–99° C.

The following compounds are obtained in an analogous manner:

(a)
1-[carbazolyl-(4)-oxy]-3-[N-methyl-2-(2-methoxyphenoxy)-ethylamino]-propan-2-ol yield 22% of theory; colorless oil; hydrochloride m.p. 109° C. (slight evolution of gas),
from 4-(2,3-epoxypropoxy)-carbazole and N-methyl-2-(2-methoxyphenoxy)-ethylamine.

(b)
1-[carbazolyl-(4)-oxy]-3-[N-butyl-2-(2-methoxyphenoxy)-ethylamino]-propan-2-ol yield 84% of theory; colorless oil; hydrochloride m.p. 169°–170° C.,
from 4-(2,3-epoxypropoxy)-carbazole and N-[2-(2-methoxyphenoxy)-ethyl]-butylamine.

(c)
1-[carbazolyl-(4)-oxy]-3-[N-benzyl-2-(5-carbamoyl-2-pyridyloxy)-ethylamino]-propan-2-ol yield 80% of theory; m.p. 165°–167° C.
from 4-(2,3-epoxypropoxy)-carbazole and N-[2-(5-carbamoyl-2-pyridyloxy)-ethyl]-benzylamine.

EXAMPLE 6
1-[Carbazolyl-(4)-oxy]-2-formyloxy-3-[N-benzyl-2-(2-methoxyphenoxy)-ethylamino]-propane hydrochloride A formic acid-acetic acid anhydride mixture prepared from 3 ml. formic acid and 6 ml. acetic anhydride is allowed to act for 2.5 days at ambient temperature on 7.9 g. 1-[carbazolyl-(4)-oxy]-3-[N-benzyl-2-(2-methoxyphenoxy)-ethylamino]-propan-2-ol. The reaction mixture is then poured into ice water, neutralized with an aqueous solution of sodium bicarbonate, extracted with methylene chloride and the desired hydrochloride then precipitated out from an ethereal solution of the extraction residue. The yield is 8.1 g. (91% of theory) of colorless crystals which sinter above 85° C. and form bubbles above 120° C.

EXAMPLE 7

1-[Carbazolyl-(4)-oxy]-2-pivaloyloxy-3-[N-benzyl-2-(2-methoxyphenoxy)-ethylamino]-propane hydrochloride 1.9 ml. pivalic acid chloride is introduced into a solution of 7.0 g. 1-[carbazolyl-(4)-oxy]-3-[N-benzyl-2-(2-methoxyphenoxy)-ethylamino]-propan-2-ol in 35 ml. pyridine. After standing overnight, the reaction mixture is poured into water, extracted with methylene chloride, purified chromatographically with a silica gel column and the hydrochloride precipitated out from an ethereal solution of the base. The yield is 6.6 g. (77% of theory) of colorless crystals which sinter above 102° C. the melt at 120° C., with a slight evolution of gas.

The following compound is prepared in an analogous manner by benzoylation:

1-[carbazolyl-(4)-oxy]-2-benzoyloxy-3-[N-benzyl-2-(2-methoxyphenoxy)-ethylamino]-propane hydrochloride Yield 70% of theory; m.p. 113° C. with slight evolution of gas.

EXAMPLE 8

1-[Carbazolyl-(4)-oxy]-2-formyloxy-3-[2-(2-methoxyphenoxy]-ethylamino]-propane hydrochloride 2.2 g. 1-[Carbazolyl-(4)-oxy]-2-formyloxy-3-[N-benzyl-2-(2-methoxyphenoxy)-ethylamino]-propane hydrochloride are hydrogenated in 40 ml. anhydrous tetrahydrofuran in the presence of 0.3 g. 10% palladium-charcoal at atmospheric pressure. After filtering with suction and evaporating the filtrate, the residue obtained is worked up with diethyl ether and crystallizes. The yield of the desired product is 1.3 g. (70% of theory) in the form of colorless crystals; m.p. 62° C., with bubble formation.

The following compounds are obtained in an analogous manner:

(a)

1-[carbazolyl-(4)-oxy]-2-pivaloyloxy-3-[2-(2-methoxyphenoxy)-ethylamino]-propane hydrochloride yield 85% of theory; m.p. 199°-201° C., with slight evolution of gas;

by the hydrogenolysis of 1-[carbazolyl-(4)-oxy]-2-pivaloyloxy-3-[N-benzyl-2-(2-methoxyphenoxy)-ethylamino]-propane hydrochloride.

(b)

1-[carbazolyl-(4)-oxy]-2-benzoyloxy-3-[2-(2-methoxyphenoxy)-ethylamino]-propane hydrochloride yield 84% of theory; m.p. 102° C., with evolution of gas;

by hydrogenolysis of 1-[carbazolyl-(4)-oxy]-2-benzoyloxy-3-[N-benzyl-2-(2-methoxyphenoxy)-ethylamino]-propane hydrochloride.

(c)

1-[carbazolyl-(4)-oxy]-3-[2-(5-carbamoyl-2-pyridyloxy)-ethylamino]-propan-2-ol m.p. 176°-178° C.;

by hydrogenolysis of 1-[carbazolyl-(4)-oxy]-3-[N-benzyl-2-(5-carbamoyl-2-pyridyloxy)-ethylamino]-propan-2-ol.

(d)

1-[carbazolyl-(4)-oxy]-3-[2-(2-hydroxyphenoxy)-ethylamino]-propan-2-ol yield 77% of theory; hydrochloride m.p. 214°-215° C.; by hydrogenolysis of 1-[carbazolyl-(4)-oxy]-3-[2-(2-benzyloxyphenoxy)-ethylamino]-propan-2-ol.

EXAMPLE 9

1-[Carbazolyl-(4)-oxy]-3-[2-(5-fluoro-2-methoxyphenoxy)-ethylamino]-propan-2-ol 7.0 g. 1-Amino-3-[carbazolyl-(4)-oxy]-propan-2-ol, 9.2 g. 2-(5-fluoro-2-methoxyphenoxy)-ethyl p-toluenesulphonate and 3.8 ml. triethylamine are stirred in 20 ml. dimethylformamide for 20 hours at 70° C. The reaction mixture is then poured into a dilute aqueous solution of sodium hydroxide, extracted with methylene chloride, dried and purified chromatographically in the manner described in Example 4. After recrystallization from ethyl acetate with the use of active charcoal and fullers' earth, there are obtained 2.7 g. (23% of theory) of the desired product in the form of colourless crystals; m.p. 146°-147° C.

The starting materials can be prepared in the following manner:

1-amino-3-[carbazolyl-(4)-oxy]-propan-2-ol 40 g. 4-(2,3-Epoxypropoxy)-carbazole are stirred with 500 ml. liquid ammonia in 2 liters methanol for 24 hours at 50° C. in an autoclave. After evaporating the reaction mixture and recrystallizing the residue from ethanol, there are obtained 31 g. of the desired product in the form of colorless crystals; m.p. 141°-143° C.

2-(5-fluoro-2-methoxyphenoxy)-ethyl p-toluenesulphonate 40.4 g. 5-Fluoro-2-methoxyphenol, 24.6 ml. 2-chloroethanol and 20.7 g. potassium hydroxide are stirred in 100 ml. dimethylformamide for 2 hours at 70° C. The reaction mixture is poured into water, extracted with methylene chloride, evaporated and the residue distilled in a high vacuum to give 11.3 g. 2-(5-fluoro-2-methoxyphenoxy)-ethanol in the form of a colourless oil which solidifies upon standing; m.p. 43°-45° C. The further reaction thereof with p-toluenesulphonic acid chloride gives the desired tosylate; m.p. 66°-68° C., recrystallized from ethanol.

EXAMPLE 10

1-[Carbazolyl-(4)-oxy]-3-[1-(2-methoxyphenoxy)-propyl-2-amino]-propan-2-ol

A mixture of 8.1 g. 1-amino-3-[carbazolyl-(4)-oxy]-propan-2-ol and 6.0 g. (2-methoxyphenoxy)-acetone in 250 ml. methanol is hydrogenated in the presence of 1.0 g. 10% palladium charcoal at 5 ats pressure and 38° C. and the crude product obtained is purified chromatographically in the manner described in Example 4. After triturating the residue obtained by evaporation of the main fraction, there are obtained 5.5 g. (41% of theory) of the desired product in the form of colorless crystals (m.p. 113°-117° C.) which is a crude diastereomeric mixture. By recrystallization from ethyl acetate and from ethanol, there is obtained therefrom a product with a constant melting point of 140°-141° C.

EXAMPLE 11

1-[Carbazolyl-(4)-oxy]-3-[3-(2-methoxyphenyl)-propylamino]-propan-2-ol

A solution of 4.4 g. 3-(2-methoxyphenyl)-propionic acid chloride in 50 ml. methylene chloride is added dropwise, with stirring, to a solution of 6.0 g. 1-amino-3-[carbazolyl-(4)-oxy]-propan-2-ol and 3.3 ml. triethylamine in 50 ml. methylene chloride at ambient temperature. After standing overnight, the reaction mixture is shaken with water and the organic phase is dried, evaporated and the residue is stirred with diethyl ether to give 8.2 g. (84% of theory) 1-[carbazolyl-(4)-oxy]-3-[3-(2-methoxyphenyl)-propionylamino]-propan-2-ol; m.p. 142°–144° C. 7.7 g. of this intermediate product are reduced with 1.5 g. lithium aluminium hydride in 100 ml. anhydrous tetrahydrofuran by boiling under reflux for 20 hours. After working up in the usual manner the oil obtained, it is purified chromatographically with a silica gel column in the manner described in Example 4. By recrystallization from toluene, with the use of active charcoal and fullers' earth, there are obtained 2.1 g. (28% of theory) of the desired product in the form of colorless crystals; m.p. 102°–104° C.

The effectiveness of the compounds of the invention as vaso-dialators and beta-receptor blocking agents are illustrated by the following tests:

(A) VASO DILATOR EXPERIMENTS

Rabbits were anesthesized with urethane and a catheter implanted in the middle ear artery (A. femoralis) for a continuous measurement of their arterial blood pressure. The blood pressure measurements were effected using an electromechanical transducer (Statham P 23 Db) and were recorded on a direct printer and utilized after calibration with a mercury manometer.

After determination of the starting value both jugular arteries (A. carotis) were occluded for two minutes and blood pressure thereby temporarily increased (CSE-reflex). The test compound was then injected at the lowest experimental dosage (0.125 mg/kg) intravenously and eight minutes later the CSE-reflex was again induced. In intervals of 15 minutes, the test compound was again injected in logarithmically increased dosage (Factor 2) and the CSE-reflex again induced.

Test compounds which under these conditions moderated the CSE-induced blood pressure increase were demonstrated to be vaso-dilators and the dosage which decreased the CSE-reflex by 30 mm Hg was determined (designated as $DE_{-30}$ mm Hg in the table below).

(B) BETA RECEPTOR BLOCKING ACTIVITY EXPERIMENTS

The heart beat frequency of rabbits was monitored via implanted electrodes and recorded on a frequency counter having a measurement time of 15 seconds. Isoprenalin was then injected intravenously via an ear vein, inducing an increase in heart beat frequency of from ca. 200 beats/min. to 330 beats/min. Subsequently, the test compounds were administered in increased dosage (as in Experiment A) intravenously and the heart frequency increase after isoprenalin treatment again recorded. The inhibition of isoprenalin tachycardia was taken as a measure of the beta-blockade activity of the test compounds. The dosage which limited the isoprenalin induced heart frequency increase to 250 beats/min. was determined for each test substance and is hereinafter designated $DE_{250}$.

The results from the above experiments A and B are set forth in the table below. The determination of the equal effectiveness dosages, i.e., $DE_{-30\ mm\ Hg}$ and $DE_{250}$, were determined on a logarithmic basis from four to six individual experiments and then the quotient of the vaso dilating dosage ($DE_{-30\ mm\ Hg}$) to the beta-blockade dosage ($DE_{250}$) was calculated. A high quotient was taken to indicate test compounds exhibiting substantially beta-blocking activity, whereas the test compounds with a quotient of about 1 were regarded as exhibiting both beta-blocking and vaso dilating activity, to a comparable degree.

| Vaso-dilating and Beta-blocking Activity of Inventive Compounds and Prior Art Materials* | | | |
|---|---|---|---|
| | $DE_{-30\ mm\ Hg}$ (vasodilat. Act.) (μg/kg i.v.) | $DE_{250}$ (β-blocking Act.) (μg/kg i.v.) | $\dfrac{DE_{-30\ mm\ Hg}}{DE_{250}}$ |
| Comparison Compounds | | | |
| 4-(3-isopropylamino-2-hydroxy-propoxy)-carbazol-hydrochloride | 630 | 5 | 126 |
| 4-(3-tert.butylamino-2-hydroxy-propoxy)-carbazol-oxalate | 280 | 2 | 140 |
| N—[3-(carbazolyl-4-oxy)-2-hydroxy-propyl]-α-amino-isobutyric acid | >12.800 | 50 | >256 |
| Inventive Compounds | | | |
| 1-[carbazolyl-(4)-oxy]-3-[2-(2-methoxy-phenoxy)-ethylamino]-propanol-(2) | 98 | 86 | 1.14 |
| 1[carbazolyl-(4)-oxy]-3-[2-(2-pyridyl)-ethylamino]-propanol-(2) | 500 | 160 | 3.12 |
| 1-[carbazolyl-(4)-oxy]-3-[1,4-benzodioxanyl-(2)-methylamino]-propanol-(2) | 260 | 2300 | 0.11 |
| 1-[carbazolyl-(4)-oxy]-3-[1-phenoxy-propyl-(2)-amino]-propanol-(2) | 1993 | 100 | 19.9 |
| 1[carbazolyl-(4)-oxy]-3-[N—methyl-2-(2-methoxyphenoxy)-ethyl-amino]-propanol-(2) | 3100 | 3180 | 0.97 |
| 1-[carbazolyl-(4)-oxy]-3-[2-(ethoxyphenoxy)-ethylamino]-propanol-(2) | 138 | 135 | 1.02 |
| 1-[carbazolyl-(4)-oxy]-3-(2-phenoxy-ethylamino)-propanol-(2) | 1336 | 130 | 10.28 |

*The comparison substances are disclosed in German Patent 22 40 599

The results indicate that the inventive compounds balance vaso dilating and beta-blocking activity to a much greater extent than do the prior art materials.

In actual administration of the inventive compounds, e.g., in the treatment of hypertension or angina pectoris, the appropriate dosage is of course dependent on the condition of the patient and the specific infirmity to be treated. In general, treatment should begin with small doses (e.g., 100 mg) and increased gradually depending upon the patient's response. The dosage can be increased at 5 to 7 day intervals until an average daily dosage of 100 to 300 mg is reached. For maintenance, 2 to 4 doses a day are usually required. These dosage levels will generally be appropriate, both for achieving a vaso dilating effect, i.e., for reducing blood pressure, and for inhibition of adrenergic beta-receptor activity.

The present invention provides pharmaceutical compositions which contain at least one of the new compounds in admixture with a solid or liquid pharmaceutical diluent or carrier and, if desired, also with odoriferous, flavoring and/or coloring materials, followed by forming into, for example, tablets or dragees or, with the addition of appropriate adjuvants, suspended or dissolved in water or oil, for example, olive oil.

It will be appreciated that the instant specification and examples are set forth by way of illustration and not limitation, and that various modifications and changes may be made without departing from the spirit and scope of the present invention.

What is claimed is:

1. Carbazolyl-(4)-oxypropanolamine compound of the formula

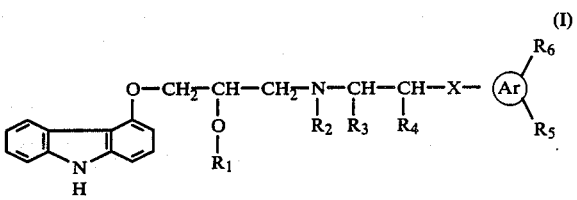

(I)

wherein
$R_1$ is hydrogen, lower alkanoyl of up to 6 carbon atoms or aroyl selected from benzoyl and naphthoyl;
$R_2$ is hydrogen, lower alkyl of up to 6 carbon atoms or arylalkyl selected from benzyl, phenylethyl and phenylpropyl;
$R_3$ is hydrogen or lower alkyl of up to 6 carbon atoms;
$R_4$ is hydrogen or lower alkyl of up to 6 carbon atoms, or when X is oxygen, $R_4$ together with $R_5$ can represent $-CH_2-O-$;
X is a valency bond, $-CH_2$, oxygen or sulfur;
Ar is selected from phenyl, naphthyl, indanyl and tetrahydronaphthyl;
$R_5$ and $R_6$ are individually selected from hydrogen, fluorine, chlorine, bromine, hydroxyl, lower alkyl of up to 6 carbon atoms, a $-CONH_2-$ group, lower alkoxy of up to 6 carbon atoms, benzyloxy, lower alkylthio of up to 6 carbon atoms, lower alkylsulphinyl of up to 6 carbon atoms and lower alkylsulphonyl of up to 6 carbon atoms; or
$R_5$ and $R_6$ together represent methylenedioxy;
and the salts thereof with physiologically acceptable acids.

2. The compound of claim 1 wherein:
$R_1$ is hydrogen, lower alkanoyl of up to 6 carbon atoms, or benzoyl;
$R_5$ and $R_6$ are individually selected from H, $OCH_3$, F, $CH_3$, $C(CH_3)_3$, $CONH_2$, OH, $OC_2H_5$, $SCH_3$, $SOCH_3$, $OCH_2C_6H_5$ or
$R_5$ and $R_6$ together represent methylenedioxy.

3. The compound of claim 2 wherein
$R_1$ is H, CHO, $COC(CH_3)_3$, $COC_6H_5$, and
$R_2$ is H or lower alkyl of up to 6 carbons.

4. The compound of claim 2 wherein
$R_1$ is H; and
X is O.

5. The compound of claim 2 wherein $R_5$ and $R_6$ are individually selected from H, $OCH_3$, $OC_2H_5$ and, together with $R_4$, $-CH_2O-$.

6. The compound of claim 5 wherein
$R_1$ is H;
$R_2$ is H or $CH_3$;
$R_3$ is H or $CH_3$;
$R_4$ is H;
Ar is phenyl;
X is O.

7. The compound of claim 1 wherein:
$R_1$ is H;
$R_2$ is H and $CH_3$;
$R_3$ is H;
$R_4$ is H;
Ar is phenyl;
X is O
$R_5$ is H, $OCH_3$ or $OC_2H_5$; and
$R_6$ is H, $OCH_3$ or $OC_2H_5$.

8. The compound as claimed in claim 1 designated 1-[carbazoyl-(4)-oxy]-3-[2-(2-methoxyphenoxy)-ethylamino]-propan-2-ol.

9. The compound as claimed in claim 1 designated 1-[carbazolyl-(4)-oxy]-3-[1,4-benzodioxanyl-(2)-methylamino]-propan-2-ol.

10. The compound as claimed in claim 1 designated 1-[carbazolyl-(4)-oxy]-3-[2-(2-ethoxyphenoxy)-ethylamino]-propan-2-ol.

11. The compound as claimed in claim 1 designated 1-[carbazolyl-(4)-oxy]-3-[N-methyl-2-(2-methoxyphenoxy)-ethylamino]-propan-2-ol.

12. A pharmaceutical composition for the treatment and prophylaxis of hypertension and/or angina pectoris comprising a pharmaceutically acceptable carrier and in therapeutically effective amounts, a carbazolyl-(4)-oxypropanolamine compound as claimed in claim 1.

13. A method of treating a subject for hypertension and/or angina pectoris which comprises administering to such subject a therapeutically effective amount of a carbazolyl-(4)-oxypropanolamine compound as claimed in claim 1.

14. The method as claimed in claim 13 wherein such compound is applied in a prophylactic manner.

15. The method as claimed in claim 13 wherein said disease is hypertension.

16. The method as claimed in claim 13 wherein said disease is angina pectoris.

17. The compound of claim 1 wherein $R_2$ is hydrogen or lower alkyl of up to 6 carbon atoms.

18. The compound of claim 1 wherein Ar is phenyl.

* * * * *

UNITED STATES PATENT AND TRADEMARK OFFICE

CERTIFICATE EXTENDING PATENT TERM
UNDER 35 U.S.C. § 156

PATENT NO.      :   4,503,067

ISSUED          :   March 5, 1985

INVENTOR(S)     :   Fritz Wiedemann, et al.

PATENT OWNER    :   Boehringer Mannheim Gmbh

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

5 years from March 5, 2002, the original expiration date of the patent, subject to the payment of maintenance fees as provided by law, with all rights pertaining thereto as provided by 35 U.S.C. § 156(b).

I have caused the seal of the Patent and Trademark Office to be affixed this 27th day of February 1998.

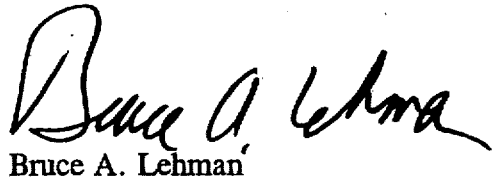

Bruce A. Lehman
Assistant Secretary of Commerce and
Commissioner of Patents and Trademarks